United States Patent
Chen

(10) Patent No.: US 11,591,629 B2
(45) Date of Patent: Feb. 28, 2023

(54) METHOD AND KIT FOR TEMPLATE-INDEPENDENT NUCLEIC ACID SYNTHESIS

(71) Applicant: Cheng-Yao Chen, Hsinchu (TW)

(72) Inventor: Cheng-Yao Chen, Hsinchu (TW)

( * ) Notice: Subject to any disclaimer, the term of this patent is extended or adjusted under 35 U.S.C. 154(b) by 331 days.

(21) Appl. No.: 16/725,420

(22) Filed: Dec. 23, 2019

(65) Prior Publication Data

US 2021/0189447 A1 Jun. 24, 2021

(51) Int. Cl.
*C12P 19/34* (2006.01)

(52) U.S. Cl.
CPC ....... *C12P 19/34* (2013.01); *C12Y 207/07007* (2013.01)

(58) Field of Classification Search
CPC ............. C12P 19/34; C12Y 207/07007; C12Y 207/07031; C12Q 2521/131
See application file for complete search history.

(56) References Cited

U.S. PATENT DOCUMENTS

2019/0264248 A1* 8/2019 Ybert ..................... C12N 15/66

OTHER PUBLICATIONS

Zuo et al. Strand annealing and terminal transferase activities of a B-family Dn A polymerase. Biochemistry (2011) 50:5379-5390.*

* cited by examiner

*Primary Examiner* — David C Thomas
(74) *Attorney, Agent, or Firm* — Hamre, Schumann, Mueller & Larson, P.C.

(57) ABSTRACT

A method for synthesizing a nucleic acid includes providing an initiator having a 3' end having an unprotected hydroxyl group, providing a nucleic acid polymerase having at least a conservative catalytic polymerase domain of a family-B DNA polymerase, providing a nucleotide monomer, and exposing the initiator to the nucleotide monomer in the presence of the nucleic acid polymerase and a metal cofactor which is a bivalent cation, and in the absence of a template, such that the nucleotide monomer is incorporated to the initiator. The kit includes the initiator, the nucleic acid polymerase, and the nucleotide monomer, and is used according to the method.

14 Claims, 3 Drawing Sheets

Specification includes a Sequence Listing.

METHOD AND KIT FOR TEMPLATE-INDEPENDENT NUCLEIC ACID SYNTHESIS

FIELD

The disclosure relates to a method and a kit for nucleic acid synthesis, more particularly to a method and a kit for template-independent nucleic acid synthesis.

BACKGROUND

De novo DNA synthesis dispensing with a DNA template has been developed during past decades. Among the currently available template-independent DNA synthesis methods, the phosphoramidite-based chemical DNA synthesis has been well-known since early 1980's, but basically has remained unchanged since then. The phosphoramidite-based chemical DNA Synthesis requires four consecutive reaction steps, including de-blocking, coupling, capping, and oxidation steps, to add one nucleoside to another nucleoside tethered to a solid support. However, one of the major drawbacks of the phosphoramidite-based chemical DNA synthesis is inevitable use of hazardous chemicals in the aforesaid reaction steps.

Due to growing demand for environmental protection, green technology applicable to DNA synthesis has drawn attention of researchers. Therefore, enzymatic DNA synthesis, which can greatly reduce use of hazardous chemicals, seems promising since such synthesis has merits such as longer strand generation, a lower error rate, a faster cycle time, a lower production cost, etc.

Speaking of template-independent enzymatic DNA synthesis, terminal deoxynucleotidyl transferase (TdT) has been found to be a template-independent DNA polymerase that adds all four deoxynucleoside triphosphates (dNTPs) to the 3' termini of DNA strands. TdT belongs to the X Family of low-fidelity DNA polymerases. The TdT-based DNA synthesis requires only two reaction steps, namely, a single-nucleotide addition by TdT and subsequent removal of the 3'-protective group from the extended 3'-end of the single-stranded DNA strand being synthesized. Even though TdT and its homologs have been applied to numerous DNA synthesis platforms, template-independent enzymatic DNA synthesis based on TdT can be hardly commercialized due to unsatisfactory product length, reagent reusability, cycle time, and so forth.

SUMMARY

Therefore, an object of the disclosure is to provide a method and a kit for synthesizing a nucleic acid, which can alleviate at least one of the drawbacks of the prior art.

The method includes providing an initiator having a 3' end having an unprotected hydroxyl group, providing a nucleic acid polymerase having at least a conservative catalytic polymerase domain of a family-B DNA polymerase, providing a nucleotide monomer, and exposing the initiator to the nucleotide monomer in the presence of the nucleic acid polymerase and a metal cofactor which is a bivalent cation, and in the absence of a template, such that the nucleotide monomer is incorporated to the initiator.

The kit includes an initiator as described above, a nucleic acid polymerase as described above, and a nucleotide monomer as described above. The kit is used according to a method as described above.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
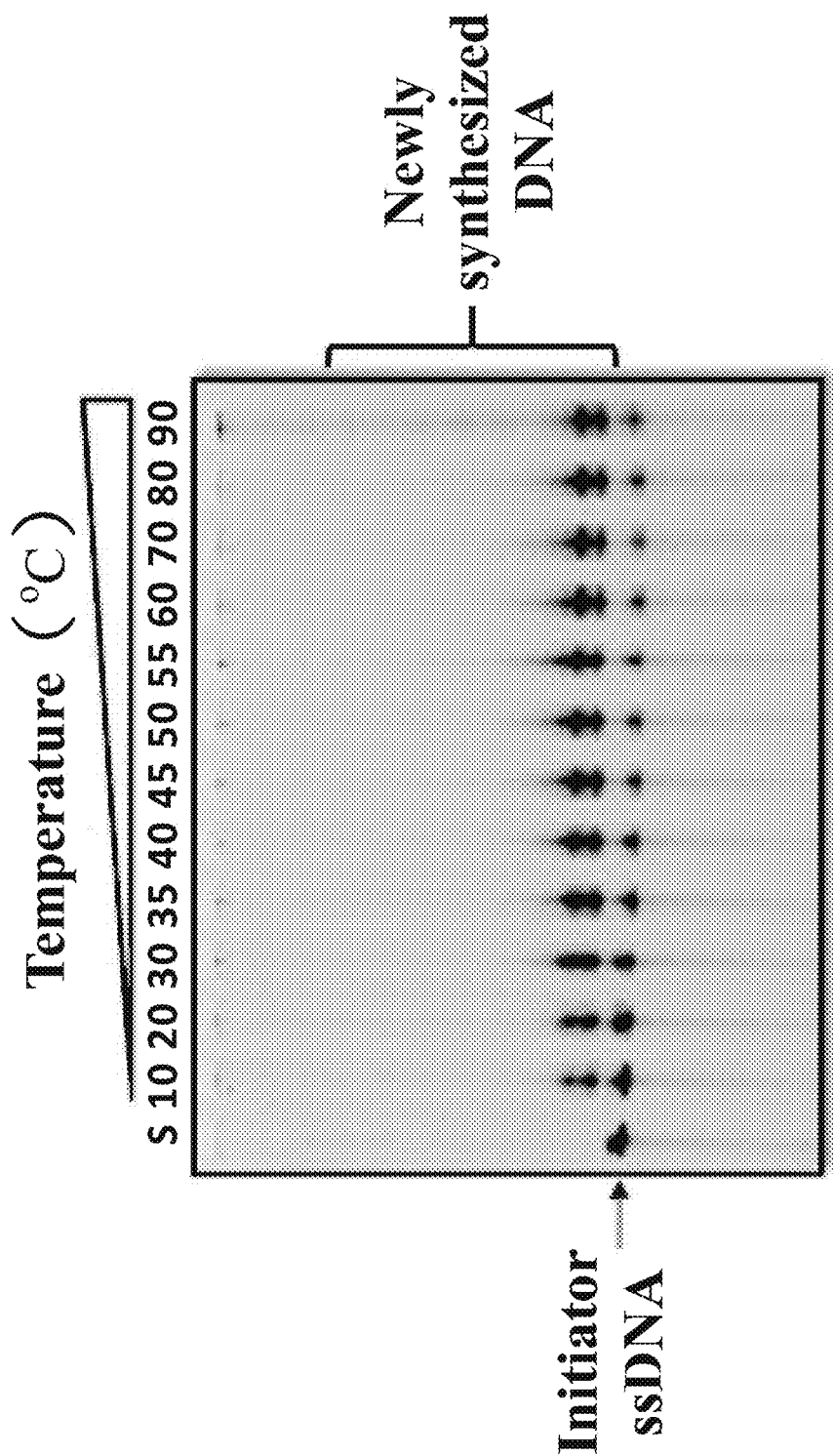
FIG. 1 is an image of denaturing urea polyacrylamide gel showing products of template-independent nucleic acid synthesis obtained at different temperatures using $KOD1^{exo-}$ DNA polymerase, in which the symbol "S" stands for substrate only.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The applicant surprisingly found that family-B DNA polymerases, which are well-known as template-dependent DNA polymerases, can be used to conduct template-independent nucleic acid synthesis (i.e. de novo nucleic acid synthesis).

Family-B DNA polymerases (also known as type-B DNA polymerases) are replicative and repair polymerases that basically have a catalytic polymerase domain and a 3' to 5' exonuclease domain, and can be found in bacteria, archaea, eukaryotes, and viruses. The term "catalytic polymerase domain" refers to a structural portion or region of the amino acid sequence of a protein which possesses the catalytic DNA/RNA polymerase activity of the protein, and which does not contain other catalytic activity, such as editing activity (e.g. proof reading activity of a 3' to 5' exonuclease domain), activity for excision of Okazaki primers during replication, and activity for interaction with other proteins. The catalytic polymerase domains of family-B DNA polymerases have a common overall architecture, which resembles a right hand and consists of thumb, palm, and fingers domains. The most conserved region is the palm domain, which contains the catalytic site.

Examples of family-B DNA polymerases include, but are not limited to, bacterial family-B DNA polymerases (e.g. Pol II), eukaryotic family-B DNA polymerases (e.g. Pol α, Pol δ, and Pol ε, and Pol ζ), archaeal family-B DNA polymerases (e.g. Pol B, Pol BI, Pol BII, and Pol BIII), and viral family-B DNA polymerases (e.g. HSV-1, RB69, T4, and Φ29).

Therefore, the present disclosure provides a method for synthesizing a nucleic acid, which includes:
providing an initiator having a 3' end having an unprotected hydroxyl group;
providing a nucleic acid polymerase having at least a conservative catalytic polymerase domain of a family-B DNA polymerase;
providing a nucleotide monomer; and
exposing the initiator to the nucleotide monomer in the presence of the nucleic acid polymerase and a metal cofactor which is a bivalent cation, and in the absence of a template, such that the nucleotide monomer is incorporated to the initiator.

The terms "nucleic acid", "nucleic acid sequence", and "nucleic acid fragment" as used herein refer to a deoxyribonucleotide or ribonucleotide sequence in single-stranded or double-stranded form, and comprise naturally occurring nucleotides or artificial chemical mimics. The term "nucleic acid" as used herein is interchangeable with the terms "oligonucleotide", "polynucleotide", "gene", "cDNA", and "mRNA" in use.

Generally, a "template" is a polynucleotide that contains the target nucleotide sequence. In some instances, the terms "target sequence", "template polynucleotide", "target nucleic acid", "target polynucleotide", "nucleic acid template", "template sequence", and variations thereof, are used interchangeably. Specifically, the term "template" refers to a strand of nucleic acid on which a complementary copy is synthesized from nucleotides or nucleotide analogs through the activity of a template-dependent nucleic acid polymerase. Within a duplex, the template strand is, by convention, depicted and described as the "bottom" strand. Similarly, the non-template strand is often depicted and described as the "top" strand. The "template" strand may also be referred to as the "sense" strand, and the non-template strand as the "antisense" strand.

The term "incorporated" or "incorporation" refers to becoming a part of a nucleic acid. There is a known flexibility in the terminology regarding incorporation of nucleic acid precursors. For example, the nucleotide dGTP is a deoxyribonucleoside triphosphate. Upon incorporation into DNA, dGTP becomes dGMP, that is, a deoxyguanosine monophosphate moiety. Although DNA does not include dGTP molecules, one may say that one incorporates dGTP into DNA.

The term "initiator" refers to a mono nucleoside, a mononucleotide, an oligonucleotide, a polynucleotide, or analogs thereof, from which a nucleic acid is to be synthesized de novo. The term "initiator" may also refer to a peptide nucleic acid (PNA).

According to the present disclosure, the initiator may have a sequence selected from a non-self complementary sequence and a non-self complementarity forming sequence. The term "self complementary" means that a sequence (e.g. a nucleotide sequence or a PNA sequence) folds back on itself (i.e. a region of the sequence binds or hybridizes to another region of the sequence), creating a double-strand like structure which can serve as a template. Depending on how close together the complementary regions of the sequence are, the strand may form, for instance, hairpin loops, junctions, bulges or internal loops. The term "self complementarity forming" is used to describe a sequence (e.g. a nucleotide sequence or a PNA sequence) from which a complementary extended portion is formed when such sequence serves as a template (namely, a self-complementary sequence is formed based on such sequence serving as a template). For instance, the self complementarity forming sequence may be "ATCC". When the "ATCC" sequence serves as a template, an extended portion "GGAT" complementary to such sequence is formed from such sequence (i.e. a self-complementary sequence "ATCCGGAT" is formed).

The term "conservative" or "conserved" is used to describe domains containing amino acid residues that are the same among a plurality of proteins having the same structure and/or function. A region of conserved amino acid residues may be important for protein structure or function. Thus, contiguous conserved amino acid residues as identified in a three-dimensional protein may be important for protein structure or function.

For instance, as reported in Albà (2001), *Genome Biology*, 2(1): reviews 3002.1 to reviews 3002.4, family-B DNA polymerases have Regions I and II that form part of the active sites of the catalytic polymerase domain, and that may respectively contain conserved amino acid residues "DT" and "SLYPS". Region I may span amino acid residues 512 to 582, amino acid residues 513 to 582 or 583, or amino acid residues 535 to 604. Region II may span amino acid residues 375 to 441 or 442, or amino acid residues 397 to 464.

According to the present disclosure, the nucleic acid polymerase may further have a 3' to 5' exonuclease domain and may be a family-B DNA polymerase selected from the group consisting of a bacterial family-B DNA polymerase, a eukaryotic family-B DNA polymerase, an archaeal family-B DNA polymerase, and a viral family-B DNA polymerase. In some embodiments, the family-B DNA polymerase is selected from the group consisting of a family-B DNA polymerase of *Thermococcus kodakaraensis* KOD1, a family-B DNA polymerase of *Pyrococus furious* (Pfu), and a family-B DNA polymerase of *Thermococcus litoralis* (Vent™).

According to the present disclosure, the 3' to 5' exonuclease domain of the family-B DNA polymerase may be inactivated. Alternatively, the 3' to 5' exonuclease activity of the family-B DNA polymerase may be reduced. Still alternatively, the 3' to 5' exonuclease domain of the family-B DNA polymerase may remain unchanged, and an inhibitor may be used to inhibit the 3' to 5' exonuclease domain of the family-B DNA polymerase during the method of the present disclosure.

According to the present disclosure, alternatively, the nucleic acid polymerase may only have the aforesaid conservative catalytic polymerase domain. In some embodiments, the nucleic acid polymerase is designed to only have the aforesaid conservative catalytic polymerase domain originally. In other embodiments, the nucleic acid polymerase was originally a family-B DNA polymerase having a 3' to 5' exonuclease domain, and such domain has been removed from the nucleic acid polymerase.

In some embodiments, the initiator is in single-stranded form.

In some embodiments, the initiator has at least five nucleotides. In an exemplary embodiment, the initiator has forty-five nucleotides.

In some embodiments, the initiator is exposed to the nucleotide monomer at a temperature ranging from 10° C. and 90° C., and/or the initiator is exposed to the nucleotide monomer at a pH of not less than 8.0 (for instance, 8.8).

According to the present disclosure, the nucleotide monomer may be a natural nucleic acid nucleotide whose constituent elements are a sugar, a phosphate group and a nitrogen base. The sugar may be ribose in RNA or 2'-deoxyribose in DNA. Depending on whether the nucleic acid to be synthesized is DNA or RNA, the nitrogen base is selected from adenine, guanine, uracil, cytosine and thymine. Alternatively, the nucleotide monomer may be a nucleotide which is modified in at least one of the three constituent elements. By way of example, the modification can take place at the level of the base, generating a modified product (such as inosine, methyl-5-deoxycytidine, deoxyuridine, dimethylamino-5-deoxyuridine, diamino-2,6-purine or bromo-5-deoxyuridine, and any other modified base which permits hybridization), at the level of the sugar (for example, replacement of a deoxyribose by an analog), or at the level of the phosphate group (for example, boronate, alkylphosphonate, or phosphorothioate derivatives).

According to the present disclosure, the nucleotide monomer may have a phosphate group selected from a monophosphate, a diphosphate, a triphosphate, a tetraphosphate, a pentaphosphate, and a hexaphosphate.

According to the present disclosure, the metal cofactor may be selected from the group consisting of $Mg^{2+}$, $Ca^{2+}$, $Sr^{2+}$, $Ba^{2+}$, $Mn^{2+}$, $Co^{2+}$, $Fe^{2+}$, $Ni^{2+}$, $Cu^{2+}$, $Zn^{2+}$, and combinations thereof. In an exemplary embodiment, the cofactor is $Mg^{2+}$. In another embodiment, the cofactor is a combination of $Mg^{2+}$ and $Mn^{2+}$.

According to the present disclosure, the nucleotide monomer may have a removable blocking moiety. Examples of the removable blocking moiety include, but are not limited to, a 3'-O-blocking moiety, a base blocking moiety, and a combination thereof.

Examples of the 3'-O-blocking moiety include, but are not limited to, O-azidomethyl, O-amino, O-allyl, O-phenoxyacetyl, O-methoxyacetyl, O-acetyl, O-(p-toluene)sulfonate, O-phosphate, O-nitrate, O-[4-methoxy]-tetrahydrothiopyranyl, O-tetrahydrothiopyranyl, O-[5-methyl]-tetrahydrofuranyl, O-[2-methyl, 4-methoxy]-tetrahydropyranyl, O-[5-methyl]-tetrahydropyranyl, and O-tetrahydrothiofuranyl, 0-2-nitrobenzyl, 0-methyl, and O-acyl.

According to the present disclosure, the base blocking moiety may be a reversible dye-terminator. Examples of the reversible dye-terminator include, but are not limited to, a reversible dye-terminator of Illumina MiSeq, a reversible dye-terminator of Illumina HiSeq, a reversible dye-terminator of Illumina Genome Analyzer IIX, and a reversible dye-terminator of Helicos Biosciences Heliscope.

According to the present disclosure, the initiator may be linked to a solid support and have a 5' end linked to the solid support. The initiator may be directly attached to the support, or may be attached to the support via a linker.

According to the present disclosure, examples of the solid support include, but are not limited to, microarrays, beads (coated or non-coated), columns, optical fibers, wipes, nitrocellulose, nylon, glass, quartz, diazotized membranes (paper or nylon), silicones, polyformaldehyde, cellulose, cellulose acetate, paper, ceramics, metals, metalloids, semiconductive materials, magnetic particles, plastics (such as polyethylene, polypropylene, and polystyrene, gel-forming materials [such as proteins (e.g., gelatins), lipopolysaccharides, silicates, agarose, polyacrylamides, methylmethracrylate polymers], sol gels, porous polymer hydrogels, nanostructured surfaces, nanotubes (such as carbon nanotubes), and nanoparticles (such as gold nanoparticles or quantum dots).

In addition, the present disclosure provides a kit for synthesizing a nucleic acid, which includes the aforesaid initiator, the aforesaid nucleic acid polymerase, and the aforesaid nucleotide monomer. The kit is used according to the method of the present disclosure.

The disclosure will be further described by way of the following examples. However, it should be understood that the following examples are solely intended for the purpose of illustration and should not be construed as limiting the disclosure in practice.

EXAMPLES

Example 1. Template-Independent Nucleic Acid Synthesis Using Family-B DNA Polymerase of *Thermococcus kodakaraensis* KOD1

A synthesis reaction mixture was prepared using suitable amounts of the following ingredients: a single-stranded initiator that had a nucleotide sequence of SEQ ID NO: 1 and a 3' end possessing an unprotected hydroxyl group and a 5' end labeled with fluorescein amidite (FAM); deoxynucleoside triphosphates (dNTPs) serving as nucleotide monomers and including dATP, dGTP, dCTP, and dTTP; a family-B DNA polymerase of *Thermococcus kodakaraensis* KOD1 that had an inactivated 3' to 5' exonuclease domain and that is referred to as $KOD1^{exo-}$ DNA polymerase; and a Tris-HCl buffer (pH 8.8). Specifically, the synthesis reaction mixture prepared contained 100 nM of the initiator, 100 μM of the dNTPs, and 200 nM of $KOD1^{exo-}$ DNA polymerase.

$KOD1^{exo-}$ DNA polymerase was prepared as follows. A gene construct encoding a family-B DNA polymerase of *Thermococcus kodakaraensis* KOD1 (intein-free and having a normal 3' to 5' exonuclease domain) was synthesized by Genomics BioSci & Tech Co. (New Taipei City, Taiwan). To obtain $KOD1^{exo-}$ DNA polymerase, the inactivation of the conservative 3' to 5' exonuclease domain was achieved by changing $Asp^{141}$ to Ala (D141A) and $Glu^{143}$ to Ala (E143A), i.e. modifying the conserved amino residues "DIE" of the conservative 3' to 5' exonuclease domain. Specifically, to accomplish the amino acid modifications "D141A" and "E143A", the corresponding nucleotide residues on the aforesaid gene construct were subjected to site-directed mutagenesis using Q5 Site-directed Mutagenesis Kit (New England Biolabs, Ipswich, Mass., USA). The resulting mutagenized gene construct was expressed in BL21(DE3) cells, and the protein expressed was purified using Akta Pure FPLC system (GE Healthcare Life Sciences, Marlborough, Mass., USA) through HisTrap Q and Heparin columns sequentially. $KOD1^{exo-}$ DNA polymerase thus obtained has an amino acid sequence of SEQ ID NO: 2.

10 μL of the synthesis reaction mixture was preincubated for 2 minutes at one of the following temperatures: 10° C., 20° C., 30° C., 35° C., 40° C., 45° C., 50° C., 55° C., 60° C., 70° C., 80° C., and 90° C. Subsequently, a suitable amount of $Mg^{2+}$ serving as cofactors were added into the respective reaction mixture to initiate the template-independent nucleic acid synthesis, which was allowed to proceed for 5 minutes. The synthesis was terminated by adding 10 μL of 2× quench solution (containing 95% de-ionized formamide and 25 mM ethylenediaminetetraacetic acid (EDTA)).

The resulting synthesis products were subjected to denaturation at 98° C. for 10 minutes. Subsequently, the synthesis products were analyzed by 15% denaturing urea polyacrylamide gel electrophoresis (Urea-PAGE). The synthesis products on the gel thus obtained were imaged using Amersham Typhoon Imager (GE Healthcare Life Sciences, Marlborough, Mass., USA).

Results:

As shown in FIG. 1, $KOD1^{exo-}$ DNA polymerase was able to perform template-independent nucleic acid synthesis at each of the temperatures tested, thereby indicating that a family-B DNA polymerase can be used to synthesize a nucleic acid in the absence of a template.

Example 2. Template-Independent Nucleic Acid Synthesis Using Family-B DNA Polymerase of *Thermococcus litoralis* (Vent™)

Template-independent nucleic acid synthesis and analysis of a resulting synthesis product were conducted generally according to the procedures set forth in Example 1, except that a family-B DNA polymerase of *Thermococcus litoralis* (Vent™) which had an inactivated 3' to 5' exonuclease domain and which is referred to as Vent$^{exo-}$ DNA polymerase was used. Vent$^{exo-}$ DNA polymerase was prepared generally in the same manner as that for preparing KOD1$^{exo-}$ DNA polymerase (see Example 1), except that a gene construct encoding a family-B DNA polymerase of *Thermococcus litoralis* (intein-free and having a normal 3' to 5' exonuclease domain) was used. Vent$^{exo-}$ DNA polymerase has an amino acid sequence of SEQ ID NO: 3.

Figure 2:
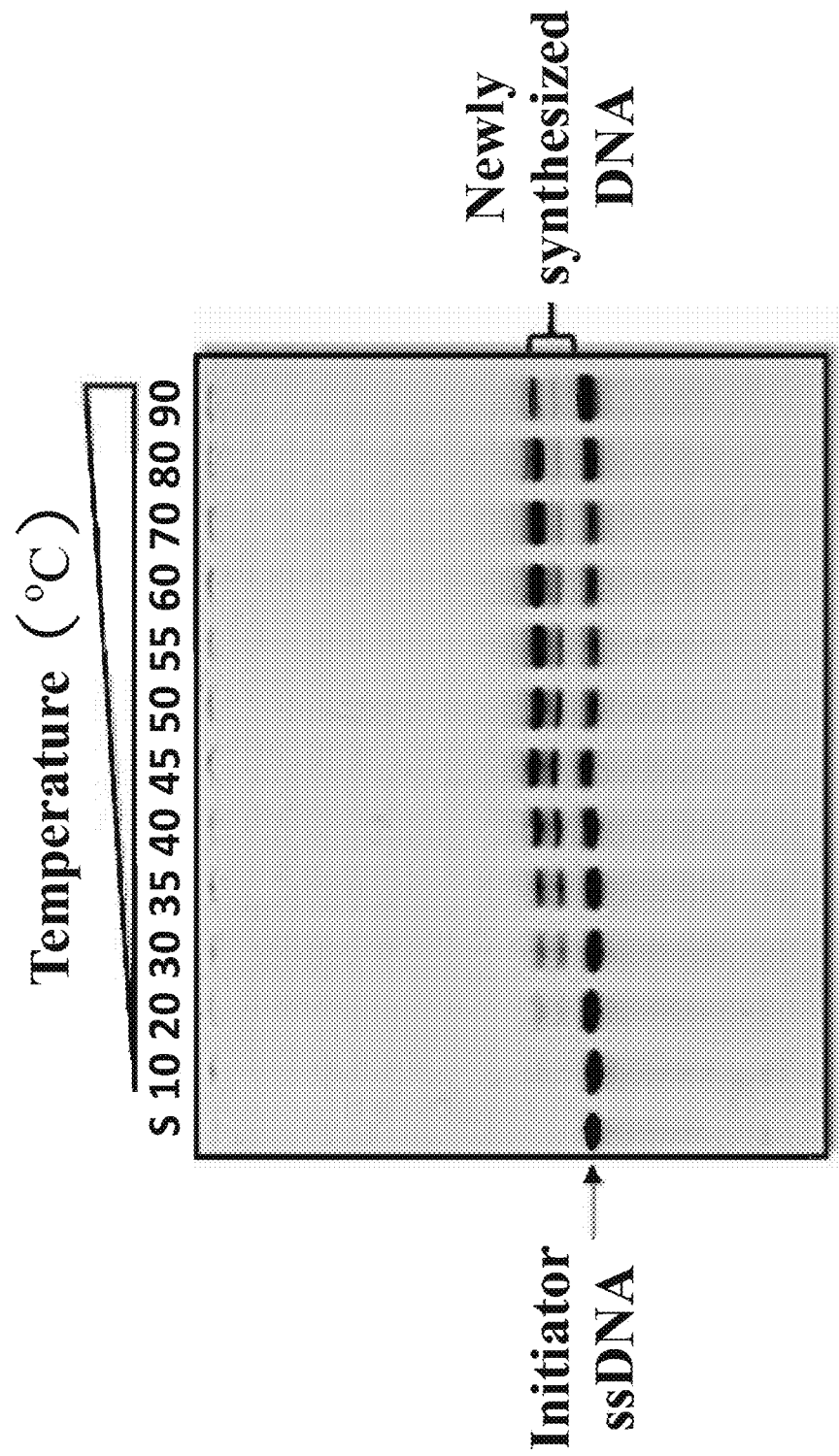
FIG. 2 is an image of denaturing urea polyacrylamide gel showing products of template-independent nucleic acid synthesis obtained at different temperatures using $Vent^{exo-}$ DNA polymerase, in which the symbol "S" stands for substrate only.

Results:

As shown in FIG. 2, Vent$^{exo-}$ DNA polymerase was able to perform template-independent nucleic acid synthesis at each of the temperatures tested, thereby indicating that a family-B DNA polymerase can be used to synthesize a nucleic acid in the absence of a template.

Example 3. Template-Independent Nucleic Acid Synthesis Using Family-B DNA Polymerase of *Pyrococus Furious* (Pfu)

Template-independent nucleic acid synthesis and analysis of a resulting synthesis product were conducted generally according to the procedures set forth in Example 1, except that a family-B DNA polymerase of Pfu which had an inactivated 3' to 5' exonuclease domain and which is referred to as Pfu$^{exo-}$ DNA polymerase was used. Pfu$^{exo-}$ DNA polymerase was prepared generally in the same manner as that for preparing KOD1$^{exo-}$ DNA polymerase (see Example 1), except that a gene construct encoding a family-B DNA polymerase of Pfu (intein-free and having a normal 3' to 5' exonuclease domain) was used. Pfu$^{exo-}$ DNA polymerase has an amino acid sequence of SEQ ID NO: 4.

Figure 3:
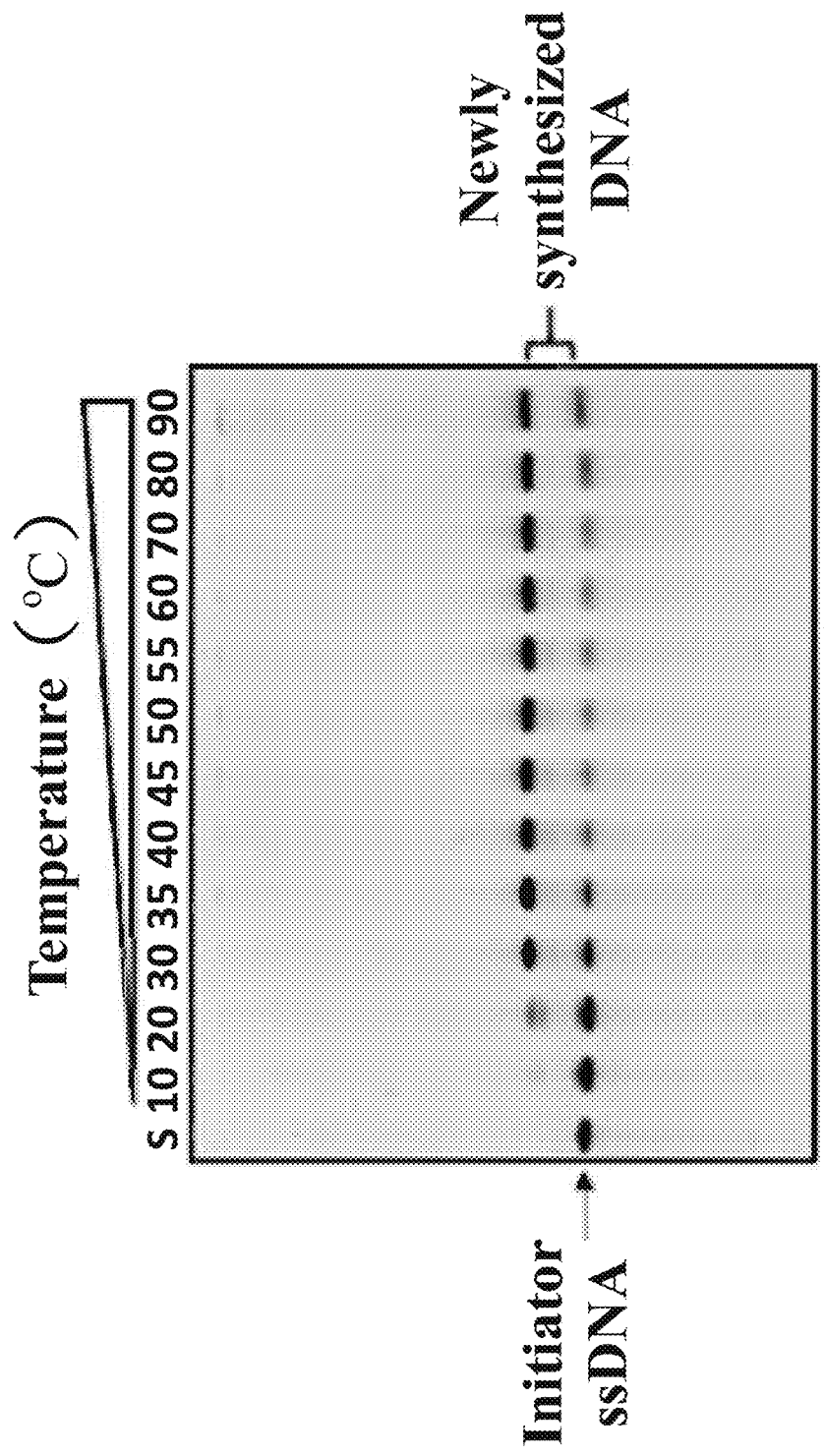
FIG. 3 is an image of denaturing urea polyacrylamide gel showing products of template-independent nucleic acid synthesis obtained at different temperatures using $Pfu^{exo-}$ DNA polymerase, in which the symbol "S" stands for substrate only.

Results:

As shown in FIG. 3, Pfu$^{exo-}$ DNA polymerase was able to perform template-independent nucleic acid synthesis at each of the temperatures tested, thereby indicating that a family-B DNA polymerase can be used to synthesize a nucleic acid in the absence of a template.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

---

What is claimed is:

1. A method for synthesizing a nucleic acid, comprising:
providing an initiator having a 3' end having an unprotected hydroxyl group;
providing a nucleic acid polymerase having at least a conservative catalytic polymerase domain of a family-B DNA polymerase;
providing a nucleotide monomer; and
exposing the initiator to the nucleotide monomer in the presence of the nucleic acid polymerase and a metal cofactor which is a bivalent cation, and in the absence of a template, such that the nucleotide monomer is incorporated to the initiator,
wherein the family-B DNA polymerase is a Thermococcaceae DNA polymerase.

2. The method of claim 1, wherein the initiator has a sequence selected from a non-self complementary sequence and a non-self complementarity forming sequence.

3. The method of claim 1, wherein the initiator is linked to a solid support and has a 5' end linked to the solid support.

4. The method of claim 3, wherein the solid support is a material selected from the group consisting of a microarray, a bead, a column, an optical fiber, a wipe, nitrocellulose, nylon, glass, quartz, a diazotized membrane, a silicone, polyformaldehyde, cellulose, cellulose acetate, paper, a ceramic, a metal, a metalloid, a semiconductor material, a magnetic particle, a plastic, a gel-forming material, a gel, a nanostructured surface, a nanotube, and a nanoparticle.

5. The method of claim 1, wherein the initiator is exposed to the nucleotide monomer at a temperature ranging from 10° C. to 90° C.

6. The method of claim 1, wherein the initiator is exposed to the nucleotide monomer at a pH of not less than 8.0.

7. The method of claim 1, wherein the metal cofactor is selected from the group consisting of $Mg^{2+}$, $Ca^{2+}$, $Sr^{2+}$, $Ba^{2+}$, $Mn^{2+}$, $Co^{2+}$, $Fe^{2+}$, $Ni^{2+}$, $Cu^{2+}$, $Zn^{2+}$ and combinations thereof.

8. The method of claim 1, wherein the family-B DNA polymerase is a *Thermococcus* or *Pyrococus* DNA polymerase.

9. The method of claim 8, wherein the family-B polymerase is selected from the group consisting of a family-B DNA polymerase of *Thermococcus kodakaraensis* KOD1, a family-B DNA polymerase of *Pyrococus furious* (Pfu), and a family-B DNA polymerase of *Thermococcus litoralis* (Vent).

10. The method of claim 1, wherein the nucleic acid polymerase further has a 3' to 5' exonuclease domain, and the 3' to 5' exonuclease domain of the family-B DNA polymerase is inactivated.

11. The method of claim 1, wherein the initiator is in single-stranded form.

12. The method of claim 1, wherein the initiator has at least five nucleotides.

13. The method of claim 1, wherein the nucleotide monomer has a phosphate group selected from the group consisting of a monophosphate, a diphosphate, a triphosphate, a tetraphosphate, a pentaphosphate, and a hexaphosphate.

14. The method of claim 1, wherein the nucleotide monomer has a removable blocking moiety selected from the group consisting of a 3'-O-blocking moiety, a base blocking moiety, and a combination thereof.

* * * * *

SEQUENCE LISTING

```
<160> NUMBER OF SEQ ID NOS: 4

<210> SEQ ID NO 1
<211> LENGTH: 45
<212> TYPE: DNA
<213> ORGANISM: Artificial Sequence
<220> FEATURE:
<223> OTHER INFORMATION: Initiator for template-independent nucleic acid
      synthesis

<400> SEQUENCE: 1
ctcggcctgg cacaggtccg ttcagtgctg cggcgaccac cgagg              45

<210> SEQ ID NO 2
<211> LENGTH: 774
<212> TYPE: PRT
<213> ORGANISM: Artificial Sequence
<220> FEATURE:
<223> OTHER INFORMATION: KOD1(exo-) DNA polymerase

<400> SEQUENCE: 2
```

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

```
Glu Val Trp Lys Leu Tyr Phe Thr His Pro Gln Asp Val Pro Ala Ile
            85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Ala Ile Ala Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
                180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495
```

```
Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
515                 520                 525

Glu Glu Lys Tyr Gly Phe Lys Val Ile Tyr Ser Asp Thr Asp Gly Phe
            530                 535                 540

Phe Ala Thr Ile Pro Gly Ala Asp Ala Glu Thr Val Lys Lys Ala
545                 550                 555                 560

Met Glu Phe Leu Lys Tyr Ile Asn Ala Lys Leu Pro Gly Ala Leu Glu
            565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
    770

<210> SEQ ID NO 3
<211> LENGTH: 774
<212> TYPE: PRT
<213> ORGANISM: Artificial Sequence
<220> FEATURE:
<223> OTHER INFORMATION: Vent(exo-) DNA polymerase

<400> SEQUENCE: 3

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45

Glu Glu Ile Lys Ala Ile Lys Gly Glu Arg His Gly Lys Thr Val Arg
        50                  55                  60

Val Leu Asp Ala Val Lys Val Arg Lys Lys Phe Leu Gly Arg Glu Val
65                  70                  75                  80
```

-continued

Glu Val Trp Lys Leu Ile Phe Glu His Pro Gln Asp Val Pro Ala Met
                 85                  90                  95
Arg Gly Lys Ile Arg Glu His Pro Ala Val Val Asp Ile Tyr Glu Tyr
            100                 105                 110
Asp Ile Pro Phe Ala Lys Arg Tyr Leu Ile Asp Lys Gly Leu Ile Pro
            115                 120                 125
Met Glu Gly Asp Glu Leu Lys Leu Leu Ala Phe Ala Ile Ala Thr
130                 135                 140
Phe Tyr His Glu Gly Asp Glu Phe Gly Lys Gly Glu Ile Ile Met Ile
145                 150                 155                 160
Ser Tyr Ala Asp Glu Glu Ala Arg Val Ile Thr Trp Lys Asn Ile
            165                 170                 175
Asp Leu Pro Tyr Val Asp Val Ser Asn Glu Arg Glu Met Ile Lys
            180                 185                 190
Arg Phe Val Gln Val Val Lys Glu Lys Asp Pro Asp Val Ile Ile Thr
            195                 200                 205
Tyr Asn Gly Asp Asn Phe Asp Leu Pro Tyr Leu Ile Lys Arg Ala Glu
    210                 215                 220
Lys Leu Gly Val Arg Leu Val Leu Gly Arg Asp Lys Glu His Pro Glu
225                 230                 235                 240
Pro Lys Ile Gln Arg Met Gly Asp Ser Phe Ala Val Glu Ile Lys Gly
            245                 250                 255
Arg Ile His Phe Asp Leu Phe Pro Val Val Arg Arg Thr Ile Asn Leu
            260                 265                 270
Pro Thr Tyr Thr Leu Glu Ala Val Tyr Glu Ala Val Leu Gly Lys Thr
            275                 280                 285
Lys Ser Lys Leu Gly Ala Glu Glu Ile Ala Ala Ile Trp Glu Thr Glu
290                 295                 300
Glu Ser Met Lys Lys Leu Ala Gln Tyr Ser Met Glu Asp Ala Arg Ala
305                 310                 315                 320
Thr Tyr Glu Leu Gly Lys Glu Phe Phe Pro Met Glu Ala Glu Leu Ala
            325                 330                 335
Lys Leu Ile Gly Gln Ser Val Trp Asp Val Ser Arg Ser Ser Thr Gly
            340                 345                 350
Asn Leu Val Glu Trp Tyr Leu Leu Arg Val Ala Tyr Ala Arg Asn Glu
            355                 360                 365
Leu Ala Pro Asn Lys Pro Asp Glu Glu Tyr Lys Arg Arg Leu Arg
    370                 375                 380
Thr Thr Tyr Leu Gly Gly Tyr Val Lys Glu Pro Glu Lys Gly Leu Trp
385                 390                 395                 400
Glu Asn Ile Ile Tyr Leu Asp Phe Arg Ser Leu Tyr Pro Ser Ile Ile
            405                 410                 415
Val Thr His Asn Val Ser Pro Asp Thr Leu Glu Lys Glu Gly Cys Lys
            420                 425                 430
Asn Tyr Asp Val Ala Pro Ile Val Gly Tyr Arg Phe Cys Lys Asp Phe
    435                 440                 445
Pro Gly Phe Ile Pro Ser Ile Leu Gly Asp Leu Ile Ala Met Arg Gln
450                 455                 460
Asp Ile Lys Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
            485                 490                 495
Tyr Gly Tyr Met Gly Tyr Pro Lys Ala Arg Trp Tyr Ser Lys Glu Cys

```
                500                 505                 510
Ala Glu Ser Val Thr Ala Trp Gly Arg His Tyr Ile Glu Met Thr Ile
            515                 520                 525

Arg Glu Ile Glu Glu Lys Phe Gly Phe Lys Val Leu Tyr Ala Asp Thr
        530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 4
<211> LENGTH: 775
<212> TYPE: PRT
<213> ORGANISM: Artificial Sequence
<220> FEATURE:
<223> OTHER INFORMATION: Pfu(exo-) DNA polymerase

<400> SEQUENCE: 4

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
```

```
                    85                  90                  95
Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Ala Ile Ala Thr
        130                 135                 140

Leu Tyr His Glu Gly Glu Phe Gly Lys Gly Pro Ile Ile Met Ile
145             150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
        210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
        290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
        370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Thr
            405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
        450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510
```

-continued

```
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
        530                 535                 540
Leu Tyr Ala Thr Ile Pro Gly Gly Glu Ser Glu Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Thr Lys
                580                 585                 590
Lys Arg Tyr Ala Val Ile Asp Glu Glu Gly Lys Val Ile Thr Arg Gly
        595                 600                 605
Leu Glu Ile Val Arg Arg Asp Trp Ser Glu Ile Ala Lys Glu Thr Gln
        610                 615                 620
Ala Arg Val Leu Glu Thr Ile Leu Lys His Gly Asp Val Glu Glu Ala
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
                660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
        690                 695                 700
Leu Arg Gly Asp Gly Pro Ile Ser Asn Arg Ala Ile Leu Ala Glu Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
                740                 745                 750
Lys Glu Asp Leu Arg Tyr Gln Lys Thr Arg Gln Val Gly Leu Thr Ser
        755                 760                 765
Trp Leu Asn Ile Lys Lys Ser
        770                 775
```